United States Patent
Hatano

(10) Patent No.: US 9,125,553 B2
(45) Date of Patent: Sep. 8, 2015

(54) ENDOSCOPE WITH ELECTRICAL CONDUCTIVE PORTION

(71) Applicant: OLYMPUS CORPORATION, Tokyo (JP)

(72) Inventor: Keisuke Hatano, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/255,148

(22) Filed: Apr. 17, 2014

(65) Prior Publication Data

US 2014/0296636 A1 Oct. 2, 2014

Related U.S. Application Data

(63) Continuation of application No. PCT/JP2013/078572, filed on Oct. 22, 2013.

(30) Foreign Application Priority Data

Mar. 5, 2013 (JP) .................................. 2013-043302

(51) Int. Cl.
*A61B 1/008* (2006.01)
*A61B 1/00* (2006.01)
(Continued)

(52) U.S. Cl.
CPC ........... *A61B 1/00124* (2013.01); *A61B 1/0008* (2013.01); *A61B 1/0011* (2013.01); *A61B 1/053* (2013.01); *A61B 1/0055* (2013.01); *A61B 1/00078* (2013.01)

(58) Field of Classification Search
CPC . A61B 1/0008; A61B 1/00124; A61B 1/0055
USPC .................................................. 600/129, 134
See application file for complete search history.

(56) References Cited

U.S. PATENT DOCUMENTS

2007/0106119 A1* 5/2007 Hirata et al. ................... 600/179
2008/0051634 A1* 2/2008 Yamashita et al. ............. 600/134
(Continued)

FOREIGN PATENT DOCUMENTS

EP 2 561 796 A1 2/2013
JP 11-344678 A 12/1999
(Continued)

OTHER PUBLICATIONS

Japanese Office Action dated Jun. 10, 2014 issued in JP 2014-517056.

*Primary Examiner* — John P Leubecker
(74) *Attorney, Agent, or Firm* — Scully, Scott, Murphy & Presser, PC

(57) ABSTRACT

A distal end bending piece subjected to processing for fastening a nail-plate portion so as to allow seesaw movements is assembled on a proximal end side of a distal end rigid portion, a sleeve is inserted from a rear side, and the sleeve is fitted and fixed to the distal end rigid portion in a state where a distal end bending piece is housed in the sleeve, thereby allowing a first nail-plate portion to elastically press an inner circumferential surface of the sleeve and allowing a second nail-plate portion to elastically press a bottom surface of a recessed portion of the distal end rigid portion at a predetermined contact pressure. Such a configuration enables a secure and stable electrical conduction between the distal end rigid portion and the distal end bending piece without interfering with a reduction in a diameter of the insertion portion.

12 Claims, 21 Drawing Sheets

(51) Int. Cl.
*A61B 1/05* (2006.01)
*A61B 1/005* (2006.01)

(56) References Cited

U.S. PATENT DOCUMENTS

2009/0093679 A1* 4/2009 Suigetsu et al. .............. 600/139
2012/0271108 A1* 10/2012 Hoshino ........................ 600/139
2013/0050457 A1 2/2013 Murayama et al.
2013/0150667 A1* 6/2013 Mitamura et al. ............ 600/104

FOREIGN PATENT DOCUMENTS

| JP | 2001-128937 A | 5/2001 |
| JP | 2004-329857 A | 11/2004 |
| JP | 5112575 B2 | 1/2013 |
| WO | WO 2012/124526 A1 | 9/2012 |

* cited by examiner

ENDOSCOPE WITH ELECTRICAL CONDUCTIVE PORTION

CROSS REFERENCE TO RELATED APPLICATION

This application is a continuation application of PCT/JP2013/078572 filed on Oct. 22, 2013 and claims benefit of Japanese Application No. 2013-043302 filed in Japan on Mar. 5, 2013, the entire contents of which are incorporated herein by this reference.

BACKGROUND OF THE INVENTION

1. Field of the Invention

The present invention relates to an endoscope which includes an insertion portion to be inserted into a subject and is configured to allow a distal end rigid portion at a distal end of the insertion portion to be electrically conductive with a conductive component coupled to the distal end rigid portion.

2. Description of the Related Art

In recent years, endoscopes including an insertion portion configured to be inserted into a subject or object have been widely used in medical fields and industrial fields. The endoscope used in the medical fields is capable of observing an organ in a body cavity by inserting an elongated insertion portion into the body cavity as a subject and performing various treatments by using, as necessary, a treatment instrument inserted into an insertion channel for the treatment instrument that is included in the endoscope. In addition, the endoscope used in the industrial fields is capable of performing examination such as observation of flaws, corrosion and the like of a region to be examined in an object and various treatments with respect to the region by inserting an elongated insertion portion of the endoscope into the object such as a jet engine or piping in a factory.

A distal end side of the insertion portion of an endoscope is constituted of a distal end rigid portion made of a rigid member such as a metal material, and the distal end rigid portion is provided with an illumination system that irradiates a subject or an object with illumination light, an image pickup unit that picks up an optical image of a site to be examined illuminated with the illumination light, and the like. The image pickup unit disposed in the distal end rigid portion is connected to a GND which is floated by being insulated from other peripheral devices connected to the endoscope, so as to ensure electrical safety, and the metal member of the distal end rigid portion is also rendered equipotential, with the potential of the GND used as a common reference electric potential.

The distal end rigid portion is connected to the GND via a bendable bending portion coupled to the proximal end side of the distal end rigid portion. The bending portion is configured by coupling a plurality of metal bending pieces, and the distal end rigid portion is connected to the GND by allowing the bending portion and the distal end rigid portion to be electrically conductive with each other. The electrical conduction between the distal end rigid portion and the bending portion is generally ensured by the structure for fitting and fixing the distal-most bending piece of the bending portion to the distal end rigid portion as disclosed in Japanese Patent Application Laid-Open Publication No. 2001-128937 or an abutting structure for allowing components to abut each other.

SUMMARY OF THE INVENTION

An endoscope according to the present invention includes: an insertion portion to be inserted into a subject; a distal end rigid portion having conductivity and disposed on a distal end side of the insertion portion in an insertion axis direction; a conductive component provided on a proximal end side of the distal end rigid portion in the insertion axis direction and coupled to the distal end rigid portion, the conductive component including an inner circumferential surface and an outer circumferential surface; an electrical conductive portion formed on the conductive component and configured to be protruded inside the inner circumferential surface or outside the outer circumferential surface, the electric conductive portion being elastically pressed against the distal end rigid portion; and an exterior member which covers the distal end rigid portion and the conductive component, and is configured to elastically press the electrical conductive portion.

DETAILED DESCRIPTION OF THE PREFERRED EMBODIMENT(S)

Hereinafter, embodiments of the present invention will be described with reference to drawings. In the respective embodiments to be described below, description will be made by taking a medical endoscope as an example. However, the present invention is applicable not only to medical endoscopes but also to industrial endoscopes.

First Embodiment

First, description will be made on the first embodiment of the present invention.

Figure 1:
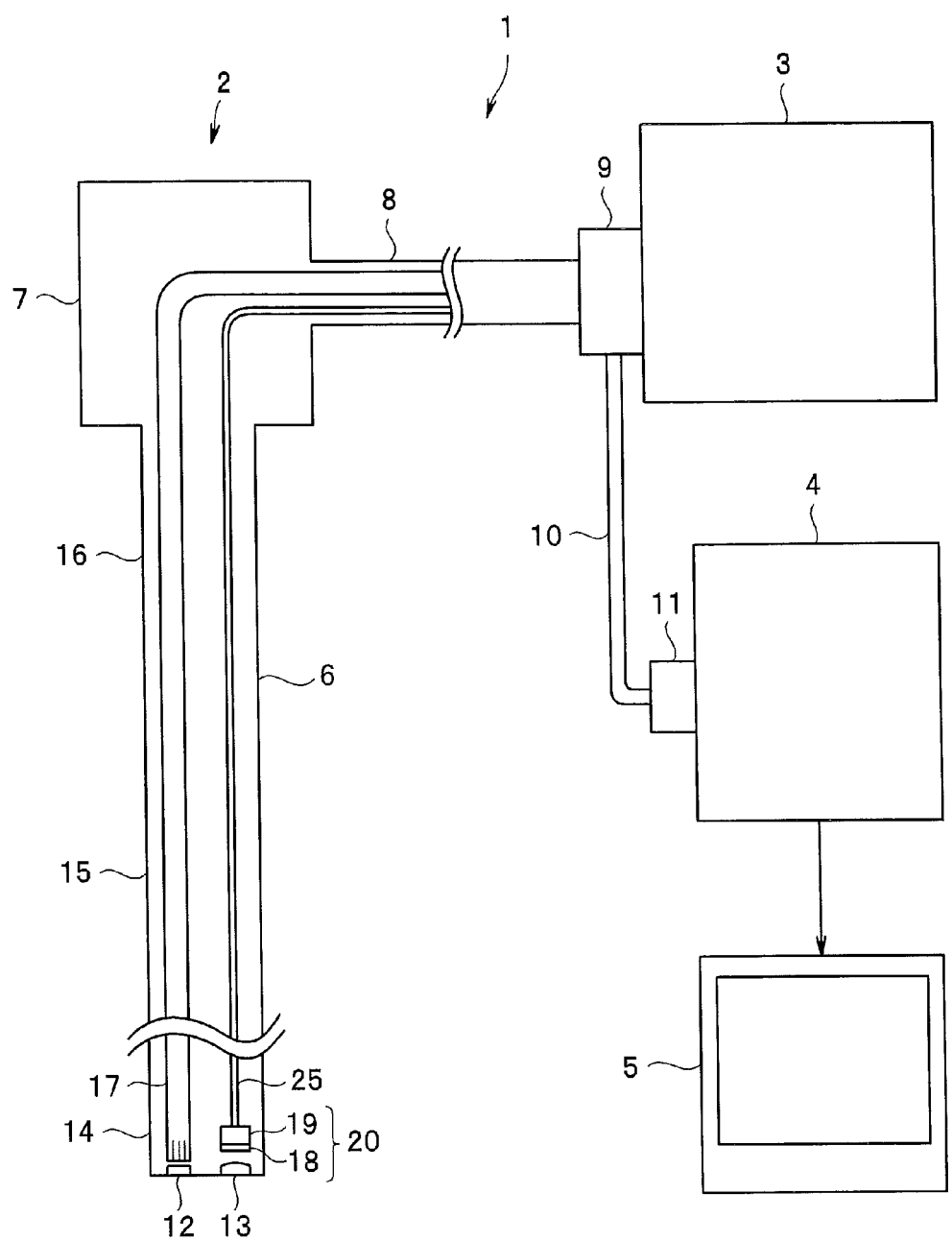
FIG. 1 relates to a first embodiment of the present invention and is a configuration diagram of an endoscope apparatus.

In FIG. 1, the reference sign 1 represents an endoscope apparatus. In the present embodiment, the endoscope apparatus 1 includes an endoscope 2 which incorporates at a distal end portion thereof an image pickup device, a light source apparatus 3 that supplies illumination light for observation to the endoscope 2, a video processor apparatus 4 that processes various signals including an image pickup signal from the endoscope 2, and a monitor 5 that receives a signal outputted from the video processor apparatus 4 to display an image of a site to be observed, or the like.

The endoscope 2 includes an elongated insertion portion 6 configured to be inserted into a subject such as a body cavity, an operation portion 7 which is connected to a proximal end portion of the insertion portion 6 in a linked manner and serves also as a grasping portion, and a universal cord 8 extended from a side surface of the operation portion 7. The universal cord 8 includes at an end portion thereof a connector 9, and the endoscope 2 is detachably connected to the light source apparatus 3 through the connector 9, and detachably connected to the video processor apparatus 4 through a connector 11 provided at an end portion of a cable 10 extended from a side portion of the connector 9.

On the distal end side of the insertion portion 6 in an insertion axis direction, a rigid distal end rigid portion 14 including an illumination optical system 12, an objective optical system 13, and the like is provided. The distal end rigid portion 14 is a rigid cylindrical frame body made of a conductive member such as a metal material, and a bending portion 15 as a movable portion which is configured to be bendable is coupled to a proximal end side of the distal end rigid portion in the insertion axis direction. Furthermore, a flexible tube portion 16, which is made of a soft tubular member and has a long length and flexibility, is provided in a linked manner at a rear portion of the bending portion 15. The bending operation of the bending portion 15 is performed through a bending operation knob, etc., disposed at the operation portion 7.

In addition, inside the insertion portion 6, a light guide 17 constituted of a fiber bundle that transmits and emits the illumination light from the light source apparatus 3 and a signal cable that transmits a signal between the endoscope and the video processor apparatus 4 are inserted, and an air/water feeding channel from which fluid is fed toward a site to be examined in a subject and a treatment instrument insertion channel from which a treatment instrument such as forceps is led out are provided. Note that sending of fluid from the air/water feeding channel is controlled by an air/water feeding apparatus (not shown) connected via the connector 9.

The light guide 17 is inserted through the insertion portion 6 to pass through inside the universal cord 8, and connected to the light source apparatus 3. The light guide 17 guides the illumination light incident from the light source apparatus 3 and emits the guided illumination light from an emission end located at the distal end of the insertion portion 6. The emission end of the light guide 17 is arranged behind the illumination optical system 12 in the distal end rigid portion 14 so as to face the illumination optical system 12, and the illumination light emitted from the illumination optical system 12 is reflected at the object such as a diseased part, to be incident from the objective optical system 13 of the distal end rigid portion 14.

Behind the objective optical system 13, an image pickup unit 20 including a solid-state image pickup device 18 such as a CCD or a CMOS disposed at an image-forming position of the objective optical system 13 and a circuit substrate portion 19 on which a circuit chip for driving the solid-state image pickup device 18 and performing processing on input and output signals is mounted, and the light from the object which is image-formed by the objective optical system 13 is photo-electrically converted by the solid-state image pickup device 18.

Figure 2:
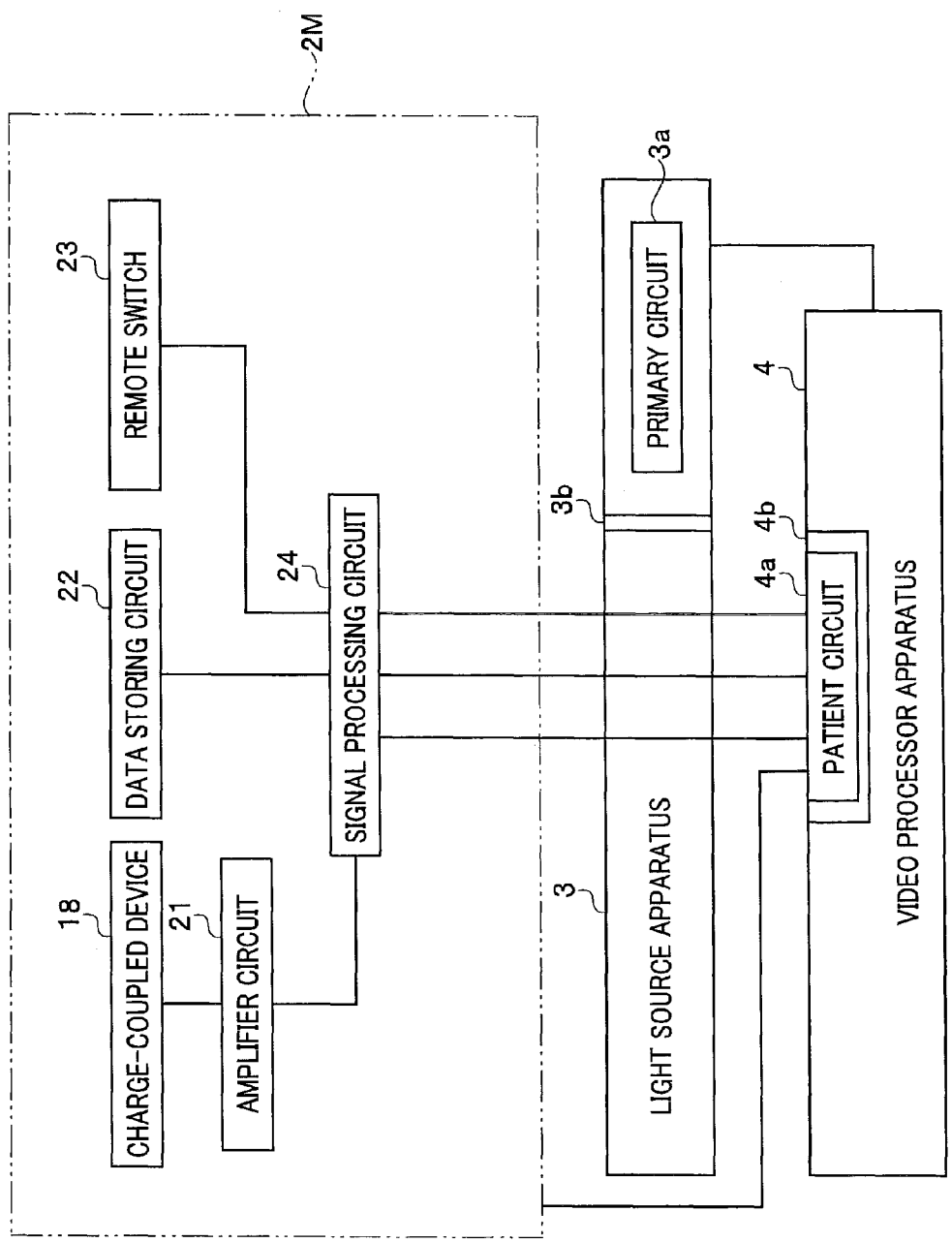
FIG. 2 relates to the first embodiment, and is a circuit block diagram showing a connection of an electric circuit system to a common potential.

As shown in FIG. 2, an amplifier circuit 21 that amplifies a signal from the solid-state image pickup device 18, a data storing circuit 22 that stores unique data such as probe identification data, and a signal processing circuit 24 that performs processing on signals from the circuits 21, 22 and a signal from a remote switch 23 of the operation portion 7, which performs remote operation such as freeze, release, image enhancement, and white balance adjustment are mounted on the circuit substrate portion 19 of the image pickup unit 20. A signal cable 25 is extended from the signal processing circuit 24, passes through the universal cord 8, the connector 9, the cable 10, and the connector 11, to be connected to the video processor apparatus 4 in the subsequent stage.

The video processor apparatus 4 is provided with a driving circuit that drives the solid-state image pickup device 18, a pre-process circuit that preprocesses the image pickup signal from the solid-state image pickup device 18, and the like, as a patient circuit 4a that forms a circuit system which is commonly used for the image pickup unit 20 of the endoscope 2 inserted into a patient. The signal processed in the pre-process circuit is sent to a post-process circuit, and subjected to a predetermined signal processing. As a result, video signals such as NTSC signals or three primary color signals of R, G and B are generated, for example. The video signals are sent to the monitor 5, and an observation image of the object picked up by the solid-state image pickup device 18 is displayed on the monitor 5.

In this embodiment, a metal member 2M disposed on the exterior and inside of the endoscope 2 is electrically connected to the GND (common reference potential) of the patient circuit 4a of the video processor apparatus 4 so as to be rendered equipotential. The patient circuit 4a of the video processor apparatus 4 is completely insulated from a primary circuit 3a of the light source apparatus 3 connected to a commercial power supply and a secondary circuit connected to peripheral devices such as the monitor 5, through a reinforced insulation portion 4b, thereby ensuring electrical safety of the endoscope 2. Note that the primary circuit 3a is completely insulated from other circuit sections through a reinforced insulation portion 3b also in the light source apparatus 3.

Figure 3:
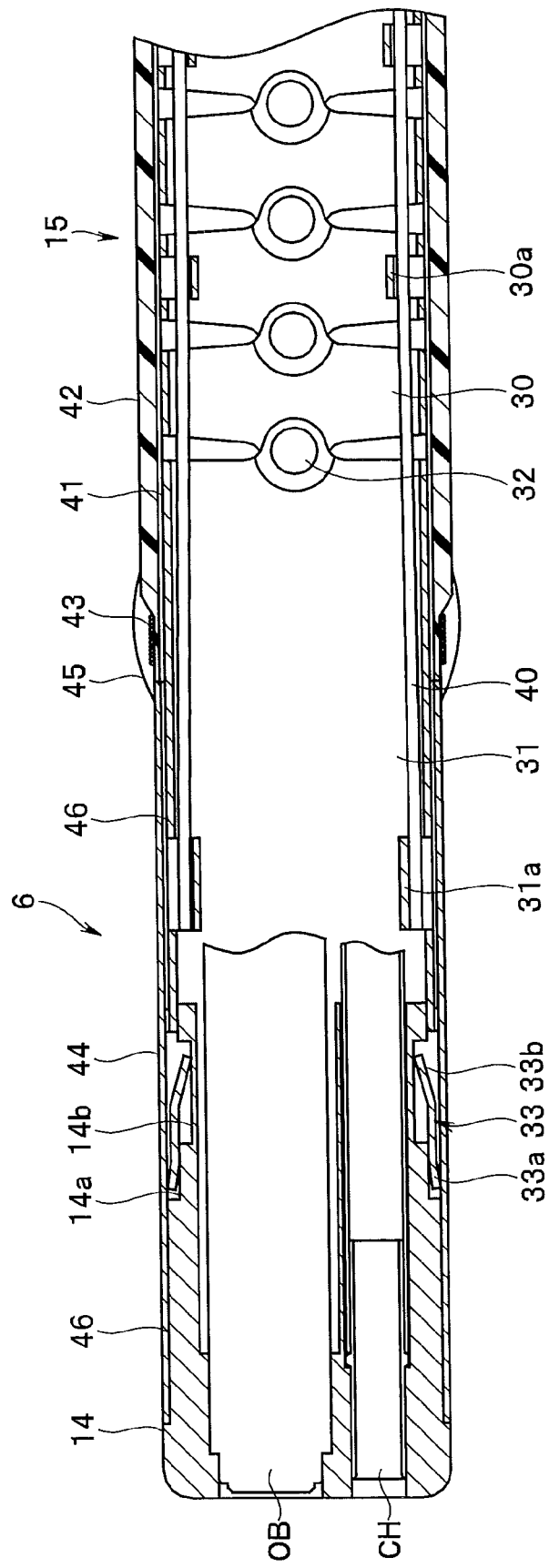
FIG. 3 relates to the first embodiment, and is an illustration diagram showing a schematic configuration of an endoscope distal end side.

The metal member 2M of the endoscope 2, which is connected to the GND of the patient circuit 4a, mainly configures the distal end rigid portion 14 of the insertion portion 6, a plurality of bending pieces 30 which constitute the bending portion 15, an operation wire 40 for bending operation, and the like, as shown in FIG. 3. As described below, the distal end rigid portion 14 and the plurality of bending pieces 30 are made of a conductive material such as stainless steel, electrically connected to each other through a distal end bending piece 31 which is the distal-most bending piece, and connected to the GND of the patient circuit 4a of the video processor apparatus 4 so as to be rendered equipotential.

Particularly, an observation system OB including the objective optical system 13 and the image pickup unit 20 is disposed in the cylindrical distal end rigid portion 14. In FIG. 3, a forceps channel CH is provided at the side portion of the observation system OB. In addition, in the observation system OB as shown in FIG. 3, the distal end lens surface of the objective optical system 13 is arranged so as to be slightly recessed lower than the distal end surface of the distal end rigid portion 14. The surface of the objective lens is thus arranged so as to be recessed lower than the distal end surface of the distal end rigid portion 14, thereby preventing a mucosa of a patient from easily adhering to the surface of the objective lens even if the distal end of the distal end rigid portion 14 contacts the mucosa, and capable of reducing the possibility that observation is interfered with.

The plurality of bending pieces 30 which constitute the bending portion 15 are configured to be bendable in two directions, i.e., up and down directions, for example, by rotatably coupling, with rivets 32, the parts where arm portions of adjacent bending pieces 30 overlap each other at a vertically corresponding positions. Note that the endoscope may include a bending portion configured to be bendable in four directions, that is, up and down directions, and left and right directions, which are perpendicular to each other. The distal end bending piece 31 coupled to the distal-most end of the plurality of bending pieces 30 is coupled and fixed to the distal end rigid portion 14, and on the inner circumferential side of the distal end bending piece 31, a wire fixing portion 31a to which each of one ends on the distal end side of a plurality of operation wires 40 is attached and fixed is provided. The wire fixing portion 31a is provided at four positions on the inner circumferential side of the distal end bending piece 31, when four operation wires 40 for four directions, that is, up, down, left and right directions are provided, for example.

The respective operation wires 40, the distal ends of which are fixed to the respective wire fixing portions 31a of the distal end bending piece 31, are inserted through circular guide rings 30a provided on the inner circumferential side of the bending pieces 30, and ends of the wires are wound respectively on sprockets coupled to a bending operation knob of the operation portion 7. According to such a configuration, when any one of the plurality of operation wires 40 is pulled with the use of the bending operation knob, the bending portion 15 bends in either the up or down direction, thereby varying the direction of observation using the observation system OB through the illumination optical system 12 of the distal end rigid portion 14 coupled to the distal end bending piece 31.

In addition, the outer circumference of the plurality of bending pieces 30 is covered with a net-like braid 41 formed by netting a metal or non-metal thin wire rods. Furthermore, the outer circumference of the braid 41 is covered with a bending rubber 42, and the bending rubber 42 forms the outer cover of the bending portion 15. The distal end part of the bending rubber 42 is fixed on the outer circumference of the distal end bending piece 31 with a spool portion 43, to be in contact with the rear end portion of a sleeve 44 fitted onto the outer circumference of the distal end rigid portion 14, and integrally fixed thereto with an adhesive 45.

The sleeve 44 is a cylindrical exterior member made of a metal material such as stainless steel and fitted to the outer circumference of the distal end rigid portion 14 so as not to generate unevenness by rendering the outer diameter of the sleeve substantially coincident with the outer diameter of the distal end rigid portion, to be fixed to the outer circumference of the distal end rigid portion with an adhesive 46. The sleeve 44 also serves as an exterior case for housing and holding inside thereof the distal end rigid portion 14 and the distal end bending piece 31, and has a function for pressing the distal end bending piece 31 against the distal end rigid portion 14 at a predetermined contact pressure, thereby surely allowing the distal end rigid portion 14 and the distal end bending piece 31 to be electrically conductive with each other.

Figure 4:
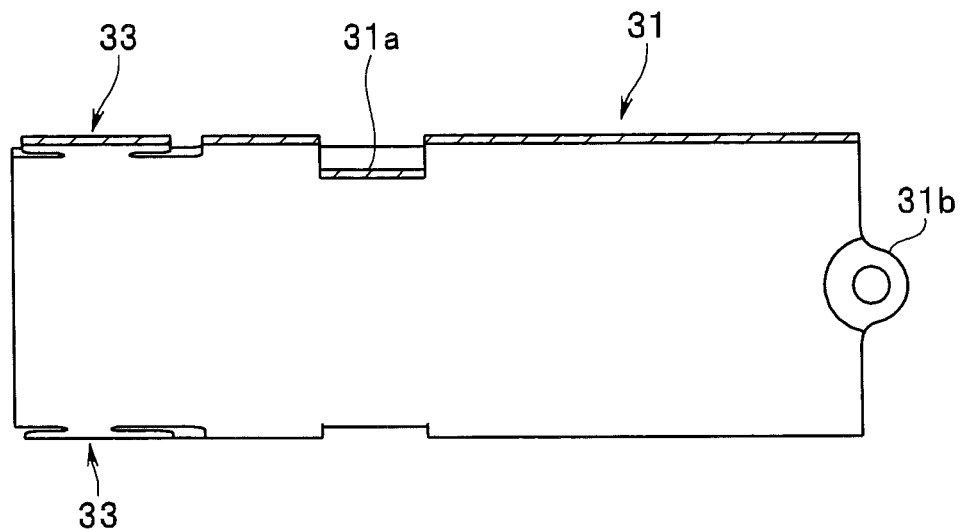
FIG. 4 relates to the first embodiment, and is an exterior view of a distal end bending piece.

Particularly, as shown in FIG. 4, the distal end bending piece 31 is formed in a substantially cylindrical shape, and includes on the proximal end side thereof an arm portion 31b coupled to the bending piece 30 through the rivet 32, and includes on the inner circumferential surface side at the middle part thereof the wire fixing portions 31a. In addition, the distal end bending piece 31 includes, at the part on the distal end side thereof, which is opposite side of the arm portion 31b across the wire fixing portions 31a, nail-plate portions 33, which form electrical conductive portions, configured to be protruded in the inner radial direction, to elastically press the outer circumference of the distal end rigid portion 14 at a predetermined contact pressure, and to allow the distal end rigid portion 14 and the bending portion 15 to be electrically conductive with each other.

In the present embodiment, the nail-plate portion 33 is provided on the distal end side of the distal end bending piece 31 in two positions opposed to each other in the radial direction in order to further ensure the electrical conduction. However, the nail-plate portion 33 has only to be provided in at least one or more positions.

Figure 5:
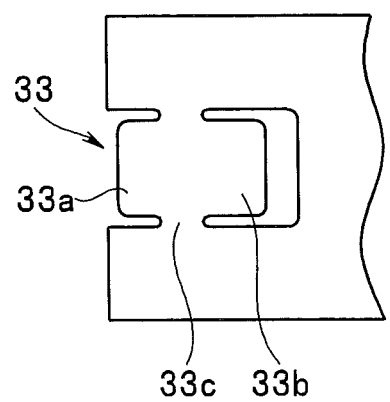
FIG. 5 relates to the first embodiment, and is an enlarged view of a nail-plate portion.

As shown in FIG. 5, each of the nail-plate portions 33 is constituted of a first nail-plate portion 33a and a second nail-plate portion 33b as two rectangular cut pieces arranged symmetrically in the insertion axis direction by forming a cutout having an "inverted square U" shape and a cutout having a "square U" shape so as to face each other in the insertion axis direction with a predetermined interval on a part of the cylindrical surface on the distal end side of the distal end bending piece 31. That is, the first nail-plate portion 33a is formed as a cut piece having an open end on the distal end side of the distal end bending piece 31, and the second nail-plate portion 33b is formed as a cut piece facing the first nail-plate portion 33a and having an open end on the rear side of the distal end bending piece. The base portion of the first nail-plate portion 33a, which is opposite side of the open end of the first nail-plate portion 33a, and the base portion of the second nail-plate portion 33b, which is opposite side of the open end of the second nail-plate portion 33b, are coupled to each other through a bridge portion 33c which joins the respective base portions like a bridge.

As shown in FIG. 3, the distal end bending piece 31 including the first and second nail-plate portions 33a, 33b thus formed is configured such that the cylindrical portion on the distal end side, which includes each of the first nail-plate portions 33a, is fitted to a small-diameter fitting portion 14a provided on the proximal end side of the distal end rigid portion 14, and the part on the proximal end side, which is more rearward than the respective nail-plate portions 33, is fixed to the inner circumferential surface of the sleeve 44 through the adhesive 46. In this configuration, the adhesive 46 is not applied to the parts corresponding to the respective nail-plate portions 33, and each of the nail-plate portions is assembled in such a manner that the first nail-plate portion 33a elastically presses the inner circumferential surface of the sleeve 44 with the open end side, and the second nail-plate portion 33b is sunk into a recessed portion 14b provided at the rear of the fitting portion 14a of the distal end rigid portion 14 such that the open end side of the second nail-plate portion elastically presses the bottom surface of the recessed portion 14b.

Here, description is made on assembling of the distal end bending piece 31 and the sleeve 44 to the distal end rigid portion 14. First, the first nail-plate portion 33a and the second nail-plate portion 33b of each of the nail-plate portions 33 are fastened with respect to the distal end bending piece 31 so as to allow seesaw movements with the bridge portion 33c as a center, and the first nail-plate portion 33a and the second nail-plate portion 33b are formed and processed such that, in the state where load is not applied in the radial direction, the open end side of the first nail-plate portion 33a is directed outward in the radial direction to protrude further than the inner circumferential surface of the sleeve 44 and the open end side of the second nail-plate portion 33b is directed inward in the radial direction to protrude further than the recessed portion 14b provided at the rear of the fitting portion 14a of the distal end rigid portion 14, and in the state where load is applied in the radial direction, the first nail-plate portion 33a and the second nail-plate portion 33b are elastically displaced.

Figure 6:
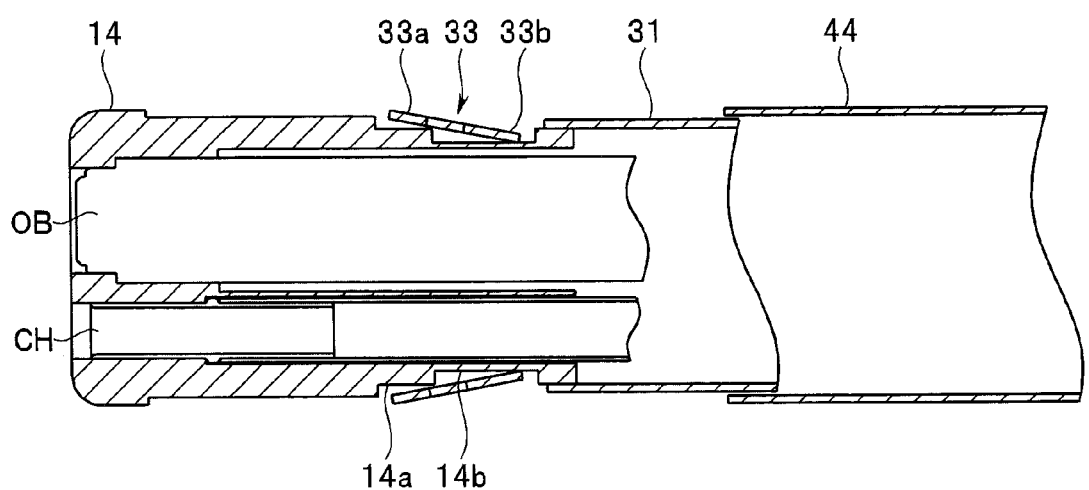
FIG. 6 relates to the first embodiment, and is an illustration diagram showing a mounting of the distal end bending piece subjected to fastening processing.

Next, the distal end bending piece 31 to which each of the nail-plate portions 33 is fastened so as to allow the seesaw movements is inserted and fitted to the proximal end side of the distal end rigid portion 14. In this state, as shown in FIG. 6, the open end of each of the first nail-plate portions 33a protrudes outward at the small-diameter fitting portion 14a provided to the distal end rigid portion 14 and each of the second nail-plate portions 33b is housed in the recessed portion 14b to allow the open end of each of the second nail-plate portions to contact the bottom surface of the recessed portion 14b. Furthermore, the sleeve 44 is inserted from the rear side of the distal end bending piece, to be fitted and fixed to the distal end rigid portion 14 in the state where the distal end bending piece 31 is housed in the sleeve 44. As a result, as shown in FIG. 3, each of the first nail-plate portions 33a elastically presses the inner circumferential surface of the sleeve 44 and each of the second nail-plate portions 33b elastically presses the bottom surface of the recessed portion 14b of the distal end rigid portion 14 at a predetermined contact pressure.

Such a configuration enables secure and stable electrical conduction among the distal end rigid portion 14, the distal end bending piece 31 and sleeve 44, to allow the insertion portion 6 to be connected to the GND of the patient circuit 4a without interfering with a reduction in the diameter of the insertion portion, and enables the electrical safety of the endoscope 2 to be ensured. In addition, the distal end bending piece 31 can be firmly fixed to the distal end rigid portion 14 only by applying the adhesive to the range excluding the nail-plate portions 33. Therefore, the stable conduction is not likely to be interfered with by the use of the adhesive.

The first nail-plate portion 33a and the second nail-plate portion 33b are symmetrically provided to the distal end bending piece 31, with the bridge portion 33c as a center. As a result, a single fastening work enables the second nail-plate portion 33b, which is to be brought into contact with the recessed portion 14b of the distal end rigid portion 14, to be bent in the inner radial direction and enables the first nail-plate portion 33a, which is to be brought into contact with the sleeve 44, to be bent in the outer radial direction, thereby facilitating the fastening work and improving working efficiency. In addition, the contact surface of the second nail-plate portion 33b, which is brought into contact with the distal end rigid portion 14, is sunk into the recessed portion 14b which is recessed lower than the rear end side outer circumferential surface of the distal end rigid portion 14, thereby allowing the open end of the second nail-plate portion 33b to be hooked on the side wall of the recessed portion 14b. As a result, the distal end bending piece is prevented from falling off.

Figure 7:
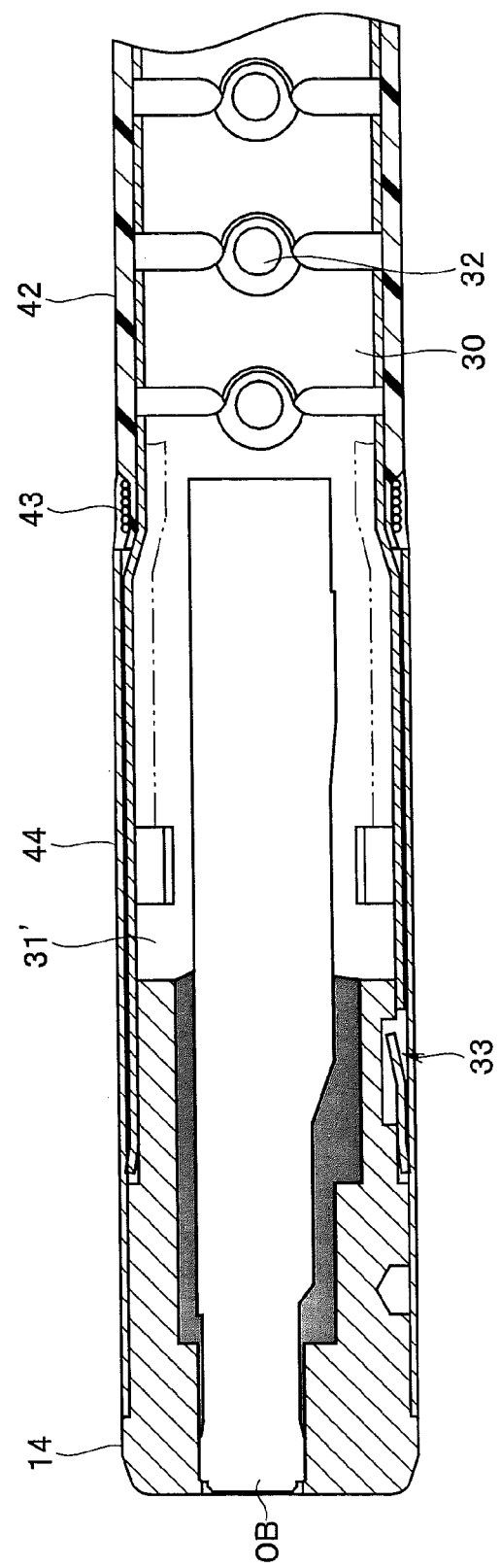
FIG. 7 relates to the first embodiment, and is an illustration diagram showing a modified example of the endoscope distal end side.

When an endoscope in which the diameter of the distal end rigid portion 14 is larger than the diameter of the bending piece 30 is used, it is preferable to use a distal end bending piece 31' having a two-stage outer diameter shape in which the diameter on the proximal end is smaller, as shown in FIG. 7, instead of the distal end bending piece 31 described above. The use of the distal end bending piece 31' thus configured enables the bending pieces 30 and the distal end rigid portion 14 having a diameter larger than that of the bending pieces 30 to be coupled with each other without using any intermediate components. In addition, in such a case, arranging the spool portion 43 that fixes the distal end part of the bending rubber 42 on the outer circumference of the small-diameter part on the proximal end side of the distal end bending piece 31' is capable of preventing the fixing portion of the bending rubber 42 from being the maximum outer diameter part of the insertion portion 6.

Figure 8:
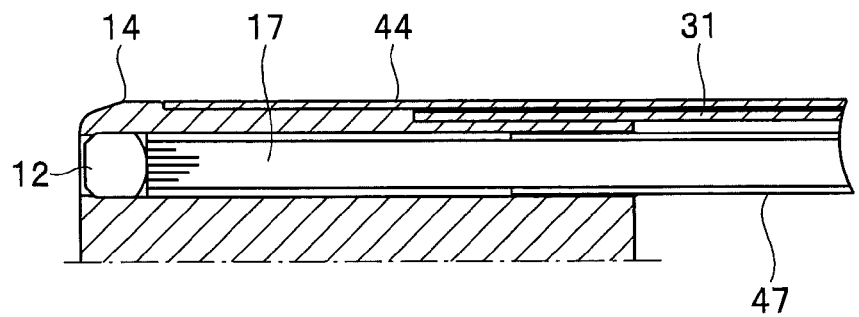
FIG. 8 relates to the first embodiment, and is an illustration diagram showing an exterior tube of a light guide.

In addition, as shown in FIG. 8, the light guide 17 inserted through the distal end rigid portion 14 is adhered and fixed to the distal end rigid portion 14, and covered with the exterior tube 47 to be inserted through the insertion portion 6. It is preferable to arrange the end portion of the exterior tube 47 on the inner side than the rear end portion of the distal end rigid portion 14, as shown in FIG. 8. With such a configuration, when the light guide 17 is adhered to the distal end rigid portion, also the exterior tube 47 can be adhered to the distal end rigid portion 14, thereby capable of preventing the fibers of the light guide 17 being exposed due to the separation of the exterior tube 47 from the fibers.

Note that FIG. 8 shows a single-system of the light guide 17 and the illumination optical system 12. However, a multiple-system of the light guides and the illumination optical systems is disposed in the insertion portion 6.

Second Embodiment

Next, the second embodiment of the present invention will be described.

Figure 9:
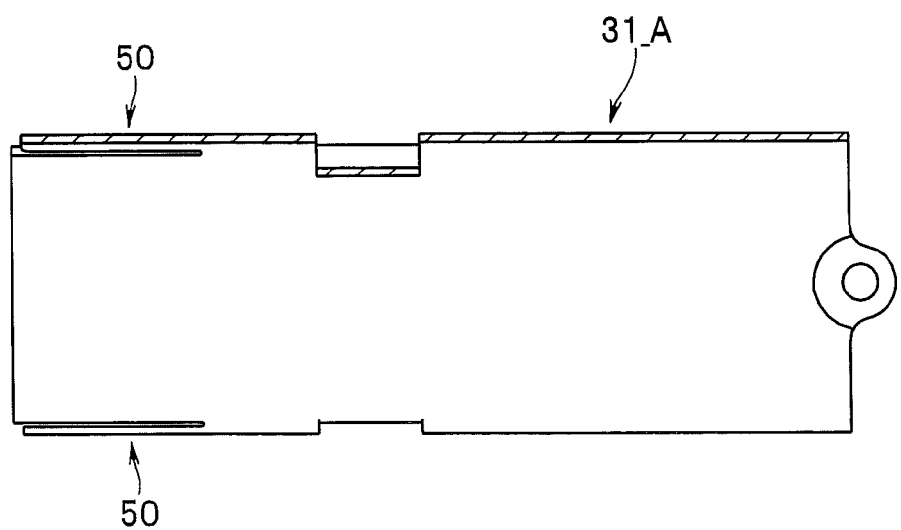
FIG. 9 relates to a second embodiment of the present invention, and is an exterior view of a distal end bending piece.

The second embodiment is an example in which a distal end bending piece 31_A as shown in FIG. 9 is employed in place of the distal end bending piece 31 according to the first embodiment. In accordance with such a modification, a distal end rigid portion 14_A in which the shape of the attaching portion is changed is used in place of the distal end rigid portion 14. Hereinafter, description will be made on the points different from the first embodiment.

Figure 10:
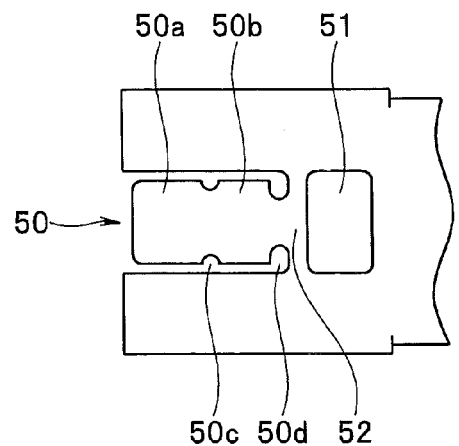
FIG. 10 relates to the second embodiment, and is an enlarged view of a nail-plate portion.

The distal end bending piece 31_A shown in FIG. 9 includes a nail-plate portion 50, which has a shape different from the nail-plate portion 33 of the distal end bending piece 31 in the first embodiment, in two positions opposed to each other in the radial direction. Particularly, as shown in FIG. 10, each of the nail-plate portions 50 includes, on the cylindrical surface on the distal end side of the distal end bending piece 31_A, two slit-like cutouts which are parallel to the insertion axis direction, and a first nail-plate portion 50a and a second nail-plate portion 50b as two rectangular cut pieces which are continuous in the insertion axis direction.

Notch portions 50c and 50d which have substantially "U" shape are provided on both sides in the width direction between the first nail-plate portion 50a on the distal end side and the second nail-plate portion 50b formed behind the first nail-plate portion 50a, and on both sides in the width direction on the proximal end side of the second nail-plate portion 50b, respectively. Furthermore, behind each of the nail-plate portions 50, a rectangular window portion 51 having substantially the same width as that of each of the nail-plate portions 50 is cut out and open.

Figure 11:
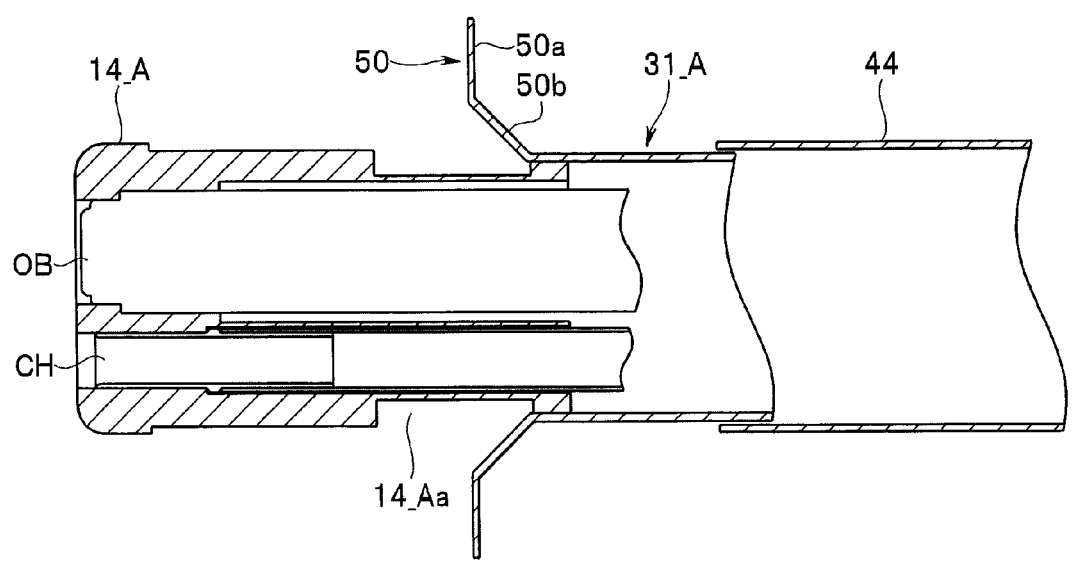
FIG. 11 relates to the second embodiment, and is an illustration diagram showing a mounting of the distal end bending piece subjected to fastening processing.

When the distal end bending piece 31_A is mounted to the distal end rigid portion 14_A, fastening work is performed in advance as shown in FIG. 11, and each of the nail-plate portions 50 is formed and processed in such a manner that the entirety of the nail-plate portion 50 is bent outward in the radial direction at the notch portion 50d located on the base portion side of the second nail-plate portion 50b, then the nail-plate portion 50 is bent at the notch portion 50c such that the first nail-plate portion 50a and the second nail-plate portion 50b protrude toward inside to form "<" shape, and, in the state where load is not applied in the radial direction, a part of the second nail-plate portion 50a protrudes further than the inner circumferential surface of the sleeve 44, and in the state where load is applied in the radial direction, the first nail-plate portion 50a and the second nail-plate portion 50bb are elastically dislocated.

In the present embodiment, the window portion 51 having the same width as that of the nail-plate portion 50 is provided on the rear end side of the nail-plate portion 50. Therefore, a bridge portion 52 formed between the second nail-plate portion 50b and the window portion 51 serves as a deform axis when the nail-plate portion 50 is fastened to be deformed, thereby capable of preventing unintended deformation.

The distal end bending piece 31_A is thus fitted onto the outer circumference of the distal end rigid portion 14_A in the state where the entirety of each of the nail-plate portions 50 of the distal end bending piece 31_A opens outward in the radial direction. Furthermore, the sleeve 44 is inserted from the rear side of the distal end bending piece, and the sleeve 44 is fitted and fixed to the distal end rigid portion 14_A in the state where the distal end bending piece 31 is housed in the sleeve 44.

Figure 12:
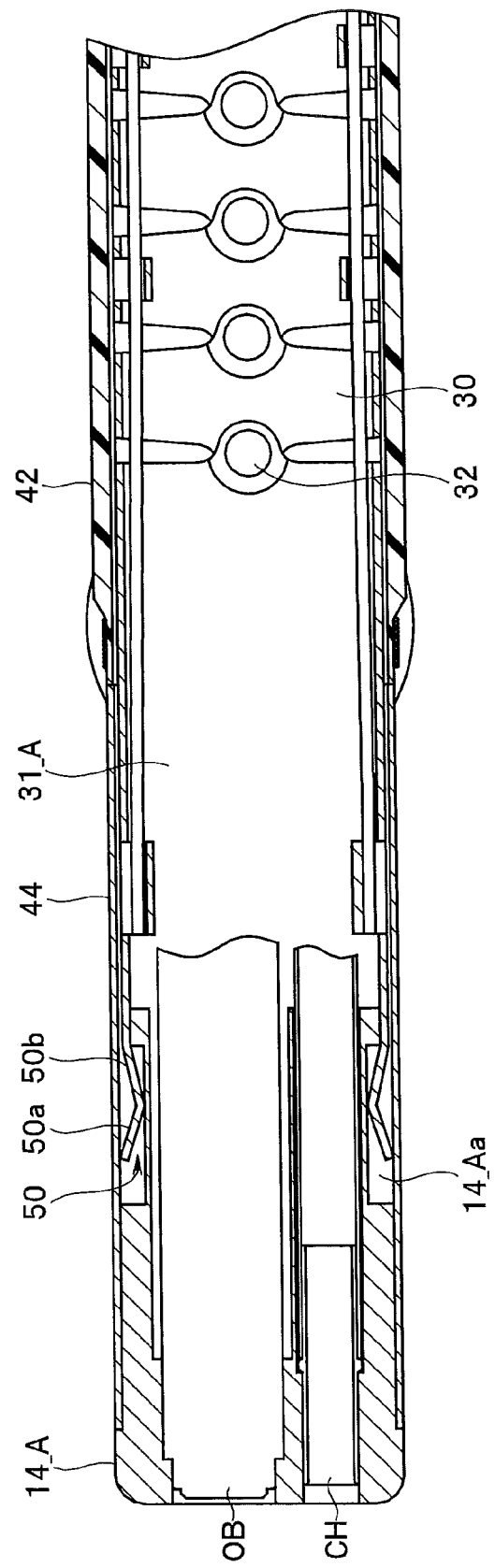
FIG. 12 relates to the second embodiment, and is an illustration diagram of an endoscope distal end side to which the distal end bending piece is mounted.

On the proximal end side of the distal end rigid portion 14_A, a recessed portion 14_Aa in which each of the first nail-plate portions 50a and each of the second nail-plate portions 50b are sunk is provided, and as shown in FIG. 12, a flexed part between the each of the first nail-plate portions 50a and each of the second nail-plate portions 50b which are bent at the notch portion 50c elastically press the bottom surface of the recessed portion 14_Aa at a predetermined contact pressure, thereby enabling each of the first nail-plate portions 50a to elastically press the inner surface of the sleeve 44. Such a configuration enables the secure and stable electrical conduction among the distal end rigid portion 14_A, the distal end bending piece 31_A, and the sleeve 44.

Figure 13:
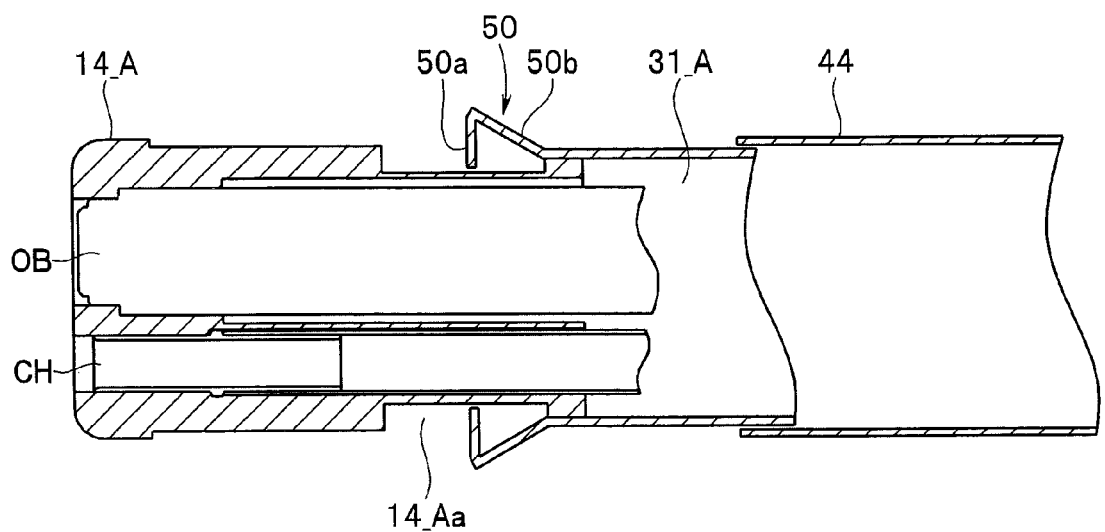
FIG. 13 relates to the second embodiment, and is an illustration diagram showing a modified example of the fastening processing of the distal end bending piece.
Figure 14:
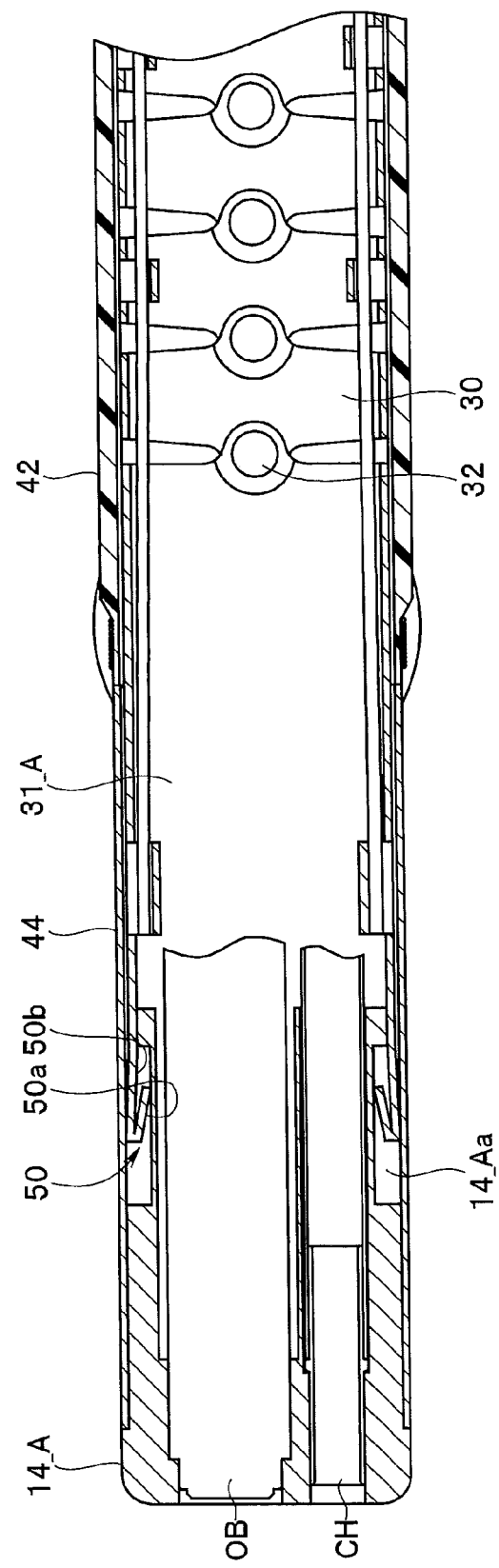
FIG. 14 relates to the second embodiment, and is an illustration diagram showing the endoscope distal end side to which the distal end bending piece subjected to the fastening processing in FIG. 13 is assembled.

The distal end bending piece 31_A may be subjected to the fastening processing as shown in FIG. 13 to be mounted to the distal end rigid portion 14_A, and electrical conduction between the distal end rigid portion 14_A and the distal end bending piece 31_A may be achieved in the manner shown in FIG. 14.

That is, as shown in FIG. 13, though the same processing is performed for bending the entirety of each of the nail-plate portions 50 of the distal end bending piece 31_A outward in the radial direction at the notch portion 50d on the base portion side of the second nail-plate portion 50b, when the first nail-plate portion 50a and the second nail-plate portion 50b are bent at the notch portion 50c, the bending processing is performed so as to form a substantially chevron shape in which the distal end side of the first nail-plate portion 50a protrudes in the radial direction.

After the distal end bending piece 31_A subjected to the fastening processing for forming each of the nail-plate portions 50 in the substantially chevron shape is mounted to the distal end rigid portion 14_A, the distal end bending piece 31_A is housed in the sleeve 44, thereby compressing the substantially chevron shape of each of the nail-plate portions 50 in the radial direction with the inner wall surface of the sleeve 44 and elastically pressing each of the first nail-plate portions 50a against the bottom surface of the recessed portion 14_Aa of the distal end rigid portion 14_A at a predetermined contact pressure, as shown in FIG. 14. As a result, the electrical conduction among the distal end rigid portion 14_A, the distal end bending piece 31_A, and the sleeve 44 is ensured. In addition, the substantially chevron shape of each of the nail-plate portions 50 is sunk into the recessed portion 14b which is recessed lower than the rear end side outer circumferential surface of the distal end rigid portion 14, thereby allowing the apex portion of the substantially chevron shape of each of the nail-plate portions 50 to be hooked on the side wall of the recessed portion 14b, which prevents the distal end bending piece from falling off.

Similarly as in the first embodiment, also the second embodiment enables the metal members disposed on the exterior and the inside of the endoscope to be surely and stably connected to the GND of the patient circuit 4a to be equipotential with the GND, without interfering with the reduction in the diameter of the insertion portion, thereby capable of securing electrical safety of the endoscope.

Third Embodiment

Next, description will be made on the third embodiment of the present invention.

Figure 15:
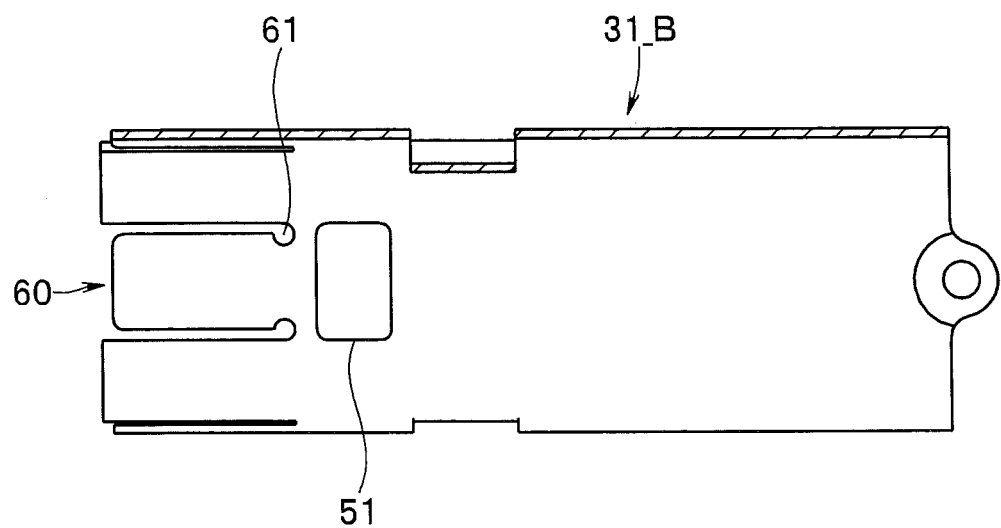
FIG. 15 relates to a third embodiment of the present invention, and is an exterior view of a distal end bending piece.

As shown in FIG. 15, the third embodiment is an example of employing a distal end bending piece 31_B, the shape of which is slightly modified from that of the distal end bending piece 31_A in the second embodiment. In accordance with the modification, a distal end rigid portion 14_B including an attaching portion whose shape is slightly changed is used in place of the distal end rigid portion 14_A. Hereinafter, description will be made on the points different from the second embodiment.

The distal end bending piece 31_B shown in FIG. 15 is modified from the distal end bending piece 31_A according to the second embodiment in that a nail-plate portion 60 as a single-shaped cut piece is used instead of sectioning the nail-plate portion 50 into the two rectangular parts, i.e., the first nail-plate portion 50a and the second nail-plate portion 50b which are continuous in the insertion axis direction. That is, two slit-like cutouts parallel to the insertion axis direction are provided on the cylindrical surface on the distal end side of the distal end bending piece 31_B, to thereby form the rectangular nail-plate portion 60 in the insertion axis direction. The nail-plate portion 60 includes a substantially "U" shaped notch portion 61 on both sides in the width direction on the proximal end side of the nail-plate portion 60, and furthermore, includes, at the rear of the nail-plate portion 60, a window portion 51 which is similar to the one in the second embodiment is cut out and open.

Figure 16:
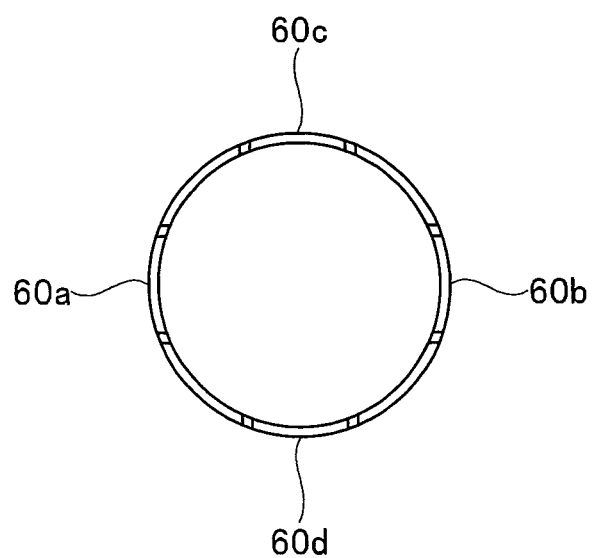
FIG. 16 relates to the third embodiment, and is a distal end side front view of the distal end bending piece.

In addition, in the third embodiment, the nail-plate portion 60 is provided equally at four sites in the circumferential direction with respect to the axis center O, as shown in FIG. 16 showing the distal end bending piece 31_B viewed from the front on the distal end side. As a matter of convenience, the nail-plate portions provided at these four sites are distinguished as nail-plate portions 60a, 60b, 60c, and 60d. As described below, the nail-plate portions are subjected to fastening processing such that one pair of nail-plate portions 60a, 60b facing each other in the rivet axis direction presses the inner circumferential surface of the sleeve 44, and another pair of nail-plate portions 60c, 60d facing each other presses the distal end rigid portion 14_B.

Figure 17:
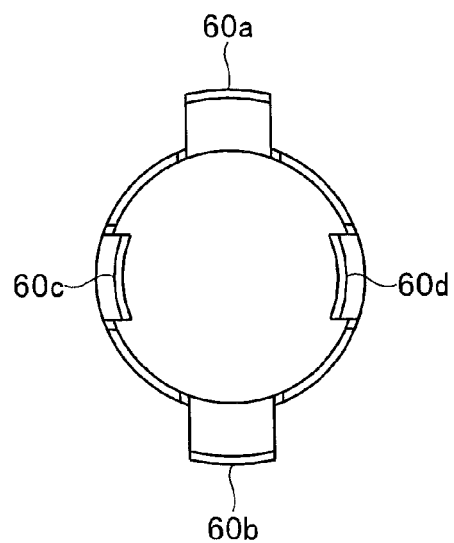
FIG. 17 relates to the third embodiment, and is a distal end side front view of the distal end bending piece subjected to fastening processing.
Figure 18:
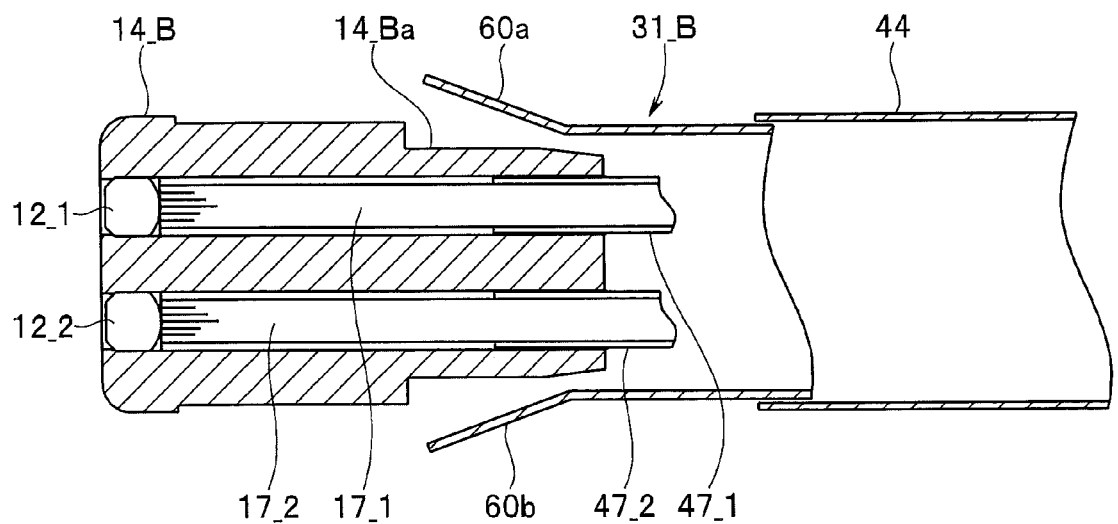
FIG. 18 relates to the third embodiment, and is an illustration diagram showing a nail-plate portion subjected to bending processing in an outer radial direction.

That is, as shown in FIGS. 17 and 18, the distal end bending piece 31_B is formed and processed by performing fastening processing in advance. The one pair of nail-plate portions 60a, 60b shown on the upper side and lower side in the drawing is bent so as to be directed outward in the radial direction, and formed and processed to be expanded such that, when load is not applied in the radial direction, the nail-plate portions protrude further than the inner circumferential surface of the sleeve 44, and when load is applied in the radial direction, the nail-plate portions are elastically displaced. On the other hand, the other pair of nail-plate portions 60c, 60d shown on the left side and right side in the drawing is bent to be narrowed so as to be directed inward in the radial direction. The distal end rigid portion 14_B includes on the proximal end side thereof a fitting portion 14_Ba having a thin diameter and a tapered end portion, and formed and processed such that, when load is not applied in the radial direction, the distal ends of the nail-plate portions 60c, 60d protrude further toward the inner radial side than the fitting portion 14_Ba, and when load is applied in the radial direction, the distal ends of the nail-plate portions 60c, 60d elastically expand.

Figure 19:
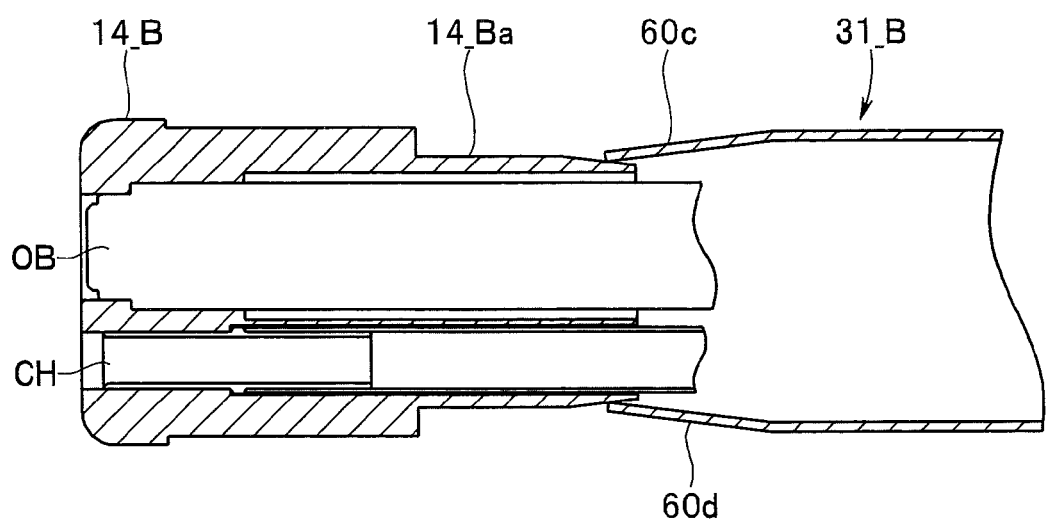
FIG. 19 relates to the third embodiment, and is an illustration diagram showing the nail-plate portion subjected to bending processing in an inner radial direction.
Figure 20:
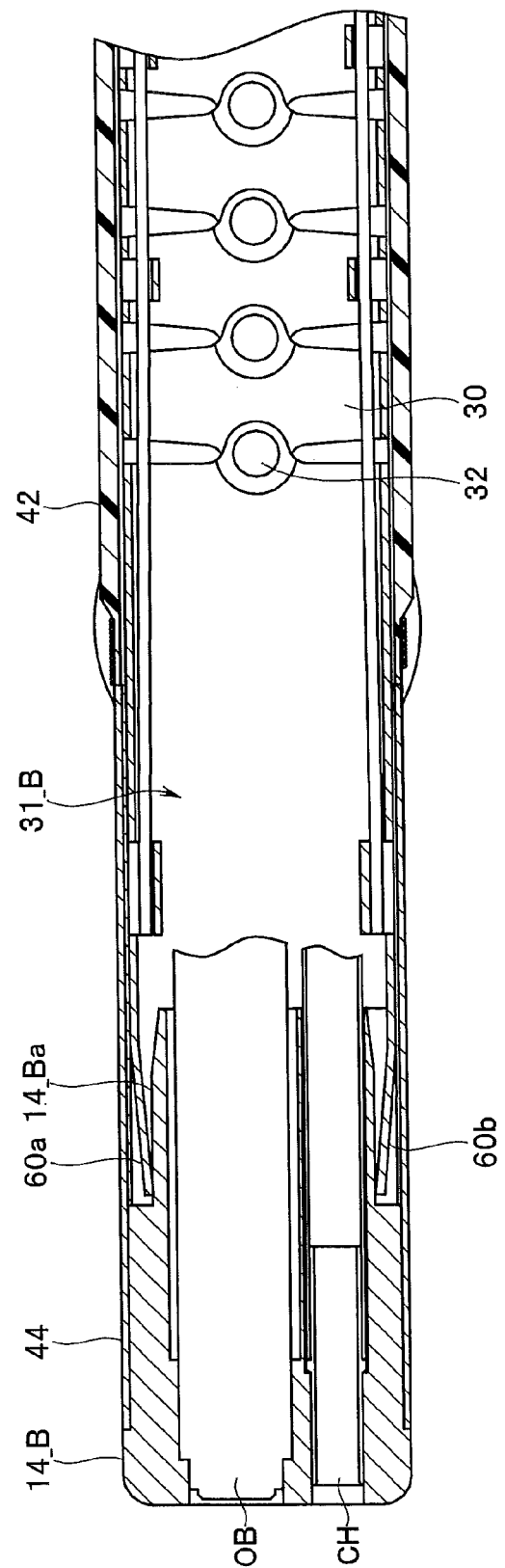
FIG. 20 relates to the third embodiment, and is an illustration diagram of the endoscope distal end side, which shows an assembled state of the nail-plate portion subjected to the bending processing in the inner radial direction.

In the above-described state, as shown in FIG. 19, the distal end bending piece 31_B is mounted to the distal end rigid portion 14_B, and the sleeve 44 is inserted in the state where the distal ends of the nail-plate portions 60c, 60d are in contact with the outer circumferential surface of the fitting portion 14_Ba of the distal end rigid portion 14_B and the nail-plate portions 60a, 60b are away from the fitting portion. As a result, as shown in FIG. 20, the proximal ends of the nail-plate portions 60c, 60d are pressed by the inner wall surface of the sleeve 44, which causes the distal end sides of the nail-plate portions 60c, 60d to elastically press the outer circumferential surface of the fitting portion 14_Ba at a predetermined contact pressure, thereby allowing the secure and stable electrical conduction among the distal end rigid portion 14_B, the distal end bending piece 31_B, and the sleeve 44.

Figure 21:
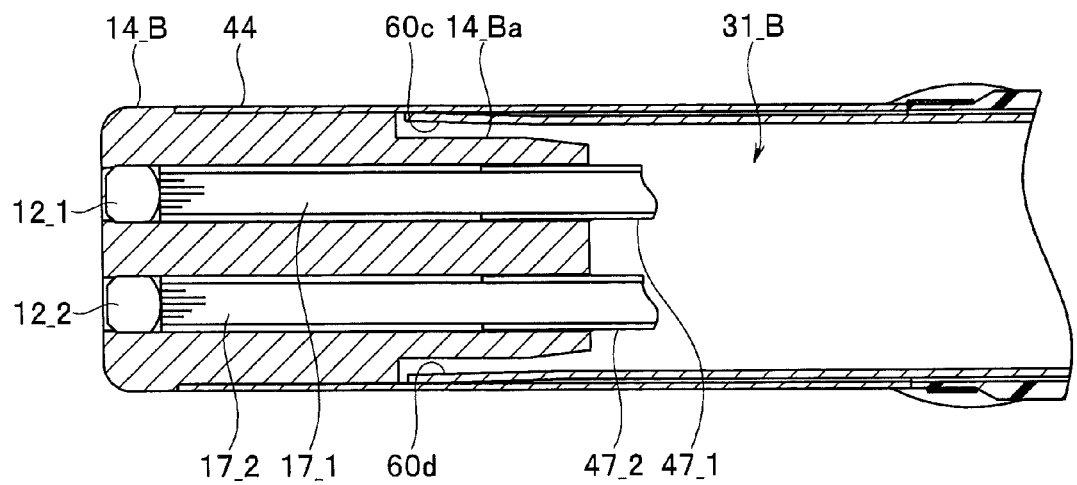
FIG. 21 relates to the third embodiment, and is an illustration diagram of the endoscope distal end side, which shows an assembled state of the nail-plate portion subjected to the bending processing in the outer radial direction.

At this time, the nail-plate portions 60a, 60b expanded in advance in the outer radial direction are pressed by the inner wall surface of the sleeve 44, as shown in FIG. 21. However, the distal end sides of the nail-plate portions 60a, 60b do not contact the outer circumferential surface of the fitting portion 14_Ba, and the nail-plate portions 60a, 60b hold the distal end bending piece 31_B with a pressing force generated between the nail-plate portions and the inner wall surface of the sleeve 44, thereby preventing the distal end bending piece 31_B from falling off.

FIGS. 18 and 21 show a dual-system illumination system constituted of a light guide 17_1 and an illumination optical system 12_1, and a light guide 17_2 and an illumination optical system 12_2. As described in the first embodiment, end portions of exterior tubes 47_1, 47_2 of the light guides 17_1, 17_2 are arranged on the inner side than the rear end portion of the distal end rigid portion 14_B to be adhered to the distal end rigid portion 14_B, thereby preventing the fibers from being exposed.

Similarly as in the above-described embodiments, also the third embodiment enables the metal members disposed on the exterior and inside of the endoscope to be surely and stably connected to the GND of the patient circuit 4a to be equipotential with the GND, without interfering with the reduction in the diameter of the insertion portion, thereby capable of ensuring the electrical safety of the endoscope.

Fourth Embodiment

Next, description will be made on the fourth embodiment of the present invention.

The fourth embodiment is an example in which the distal end bending piece 31_B according to the third embodiment is modified by changing the shape of the nail-plate portions 60c, 60d which are brought into contact with the fitting portion 14_Ba of the distal end rigid portion 14_B. The other pairs of the nail-plate portions 60a, 60b has the same shape as that in the third embodiment.

Figure 22:
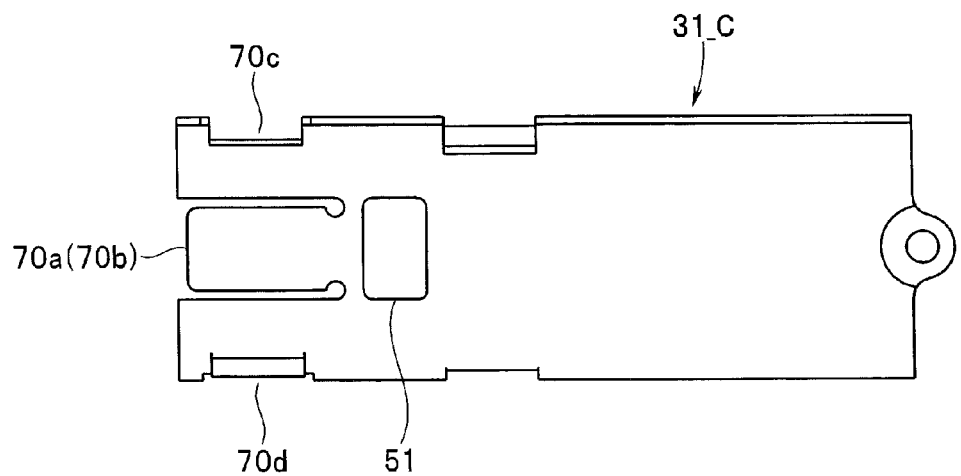
FIG. 22 relates to a fourth embodiment of the present invention, and is an exterior view of a distal end bending piece.

That is, as shown in FIG. 22, a distal end bending piece 31_C of the fourth embodiment includes one pair of nail-plate portions 70a, 70b facing each other in the rivet axis direction, which is formed to have the same shape as that of the nail-plate portions 60a, 60b in the third embodiment. Similarly, a rectangular window portion 51 is provided at the rear of each of the nail-plate portions 70a, 70b.

Figure 23:
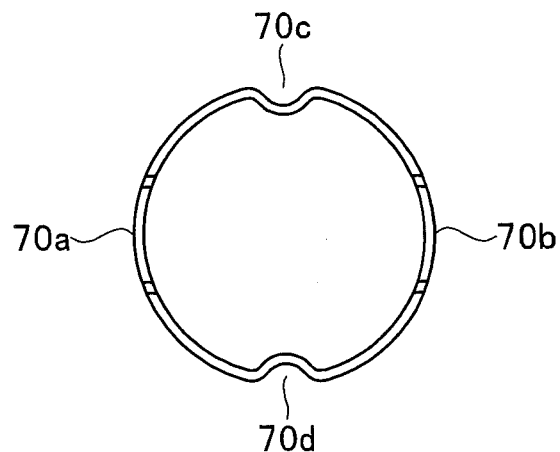
FIG. 23 relates to the fourth embodiment, and is a distal end side front view of the distal end bending piece.
Figure 24:
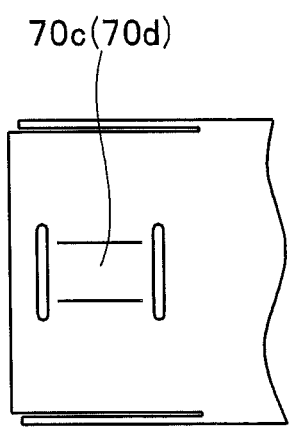
FIG. 24 relates to the fourth embodiment, and is an illustration diagram showing a nail-plate portion between slit-like cutouts.

On the other hand, as shown in FIGS. 23 and 24, the nail-plate portions 70c, 70d, which are arranged substantially perpendicularly to the nail-plate portions 70a, 70b of the distal end bending piece 31_C, are formed as protruding portions by providing two slit-like cutouts having a predetermined length and parallel to the circumferential direction on the cylindrical surface on the distal end side of the distal end bending piece 31_C and by causing the wall surface between the two slit-like cutouts to protrude in an arch shape toward inner radial side.

Figure 25:
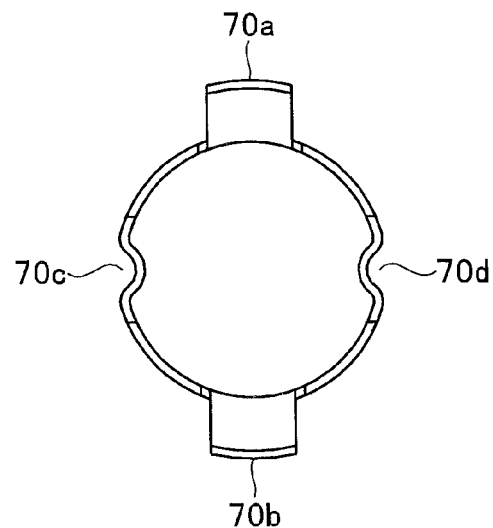
FIG. 25 relates to the fourth embodiment, and is a distal end side front view of the distal end bending piece subjected to fastening processing.
Figure 26:
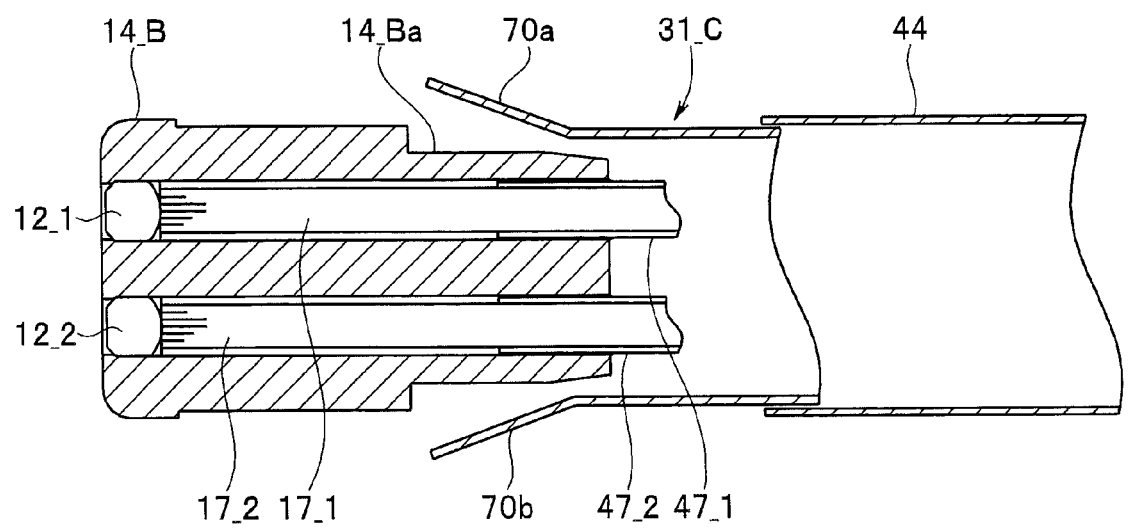
FIG. 26 relates to the fourth embodiment, and is an illustration diagram showing mounting of the nail-plate portion subjected to bending processing in an outer radial direction.

As shown in FIGS. 25 and 26, the distal end bending piece 31_C having the nail-plate potion 70 (70a, 70b, 70c, and 70d) thus configured is formed such that one pair of nail-plate portions 70a, 70b shown on the upper side and lower side in the drawings are formed and processed in the same manner as that of the nail-plate portions 60a, 60b in the third embodiment, to be bent, deformed and expanded in advance so as to be directed outward in the radial direction. The other pair of nail-plate portions 70c, 70d is subjected to deformation processing for bending the nail-plate portions slightly toward the inner radial side while maintaining the state allowing elastic expansion in the radial direction, when the distance between the apex portions protruding inner radial side is larger than the outer diameter of the fitting portion 14_Ba of the distal end rigid portion 14_B. However, when the nail-plate portions 70c, 70d are formed in advance such that the distance between the apex portions is smaller than the outer diameter of the fitting portion 14_Ba of the distal end rigid portion 14_B while maintaining the state allowing elastic expansion in the radial direction, no additional preparation work is required.

Figure 27:
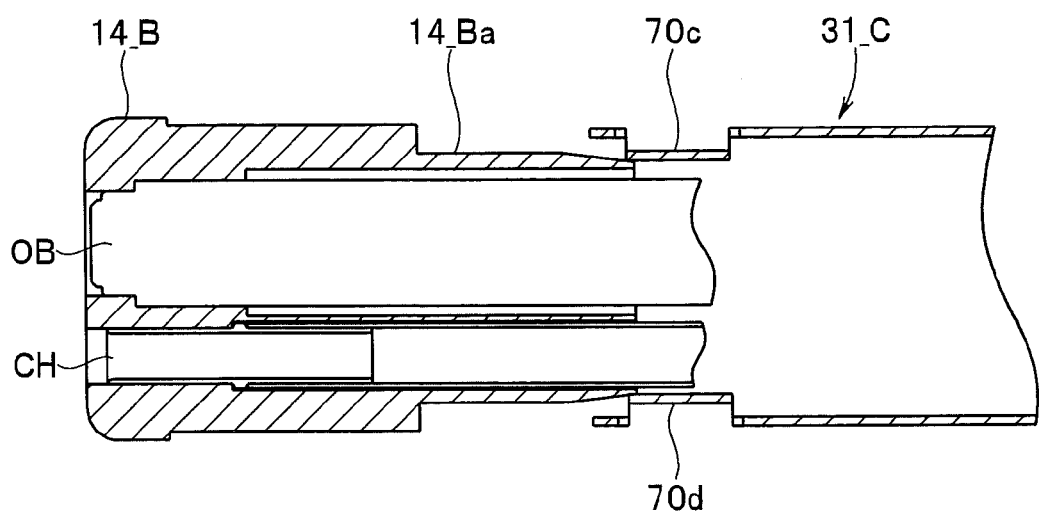
FIG. 27 relates to the fourth embodiment, and is an illustration diagram showing mounting of the nail-plate portion protruded in an inner radial direction.
Figure 28:
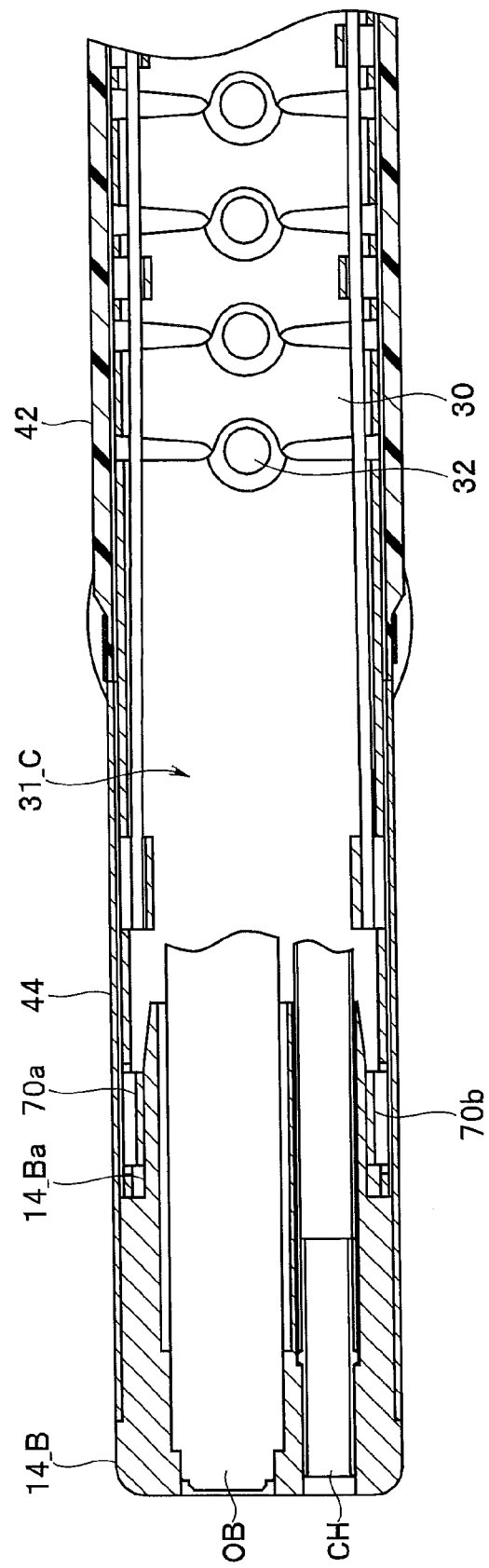
FIG. 28 relates to the fourth embodiment, and is an illustration diagram of the endoscope distal end side, which shows an assembled state of the nail-plate portion protruded in the inner radial direction.

In the above-described state, as shown in FIG. 27, the distal end bending piece 31_C is mounted to the distal end rigid portion 14_B, the apex portions on the inner radial sides of the nail-plate portions 70c, 70d are brought into contact with the distal end rigid portion 14_B, and then the sleeve 44 is inserted. As a result, as shown in FIG. 28, the apex portions on the inner radial sides of the nail-plate portions 70c, 70d elastically press the outer circumferential surface of the fitting portion 14_Ba at a predetermined contact pressure, thereby achieving the secure electrical conduction among the distal end rigid portion 14_B, the distal end bending piece 31_C, and the sleeve 44.

Figure 29:
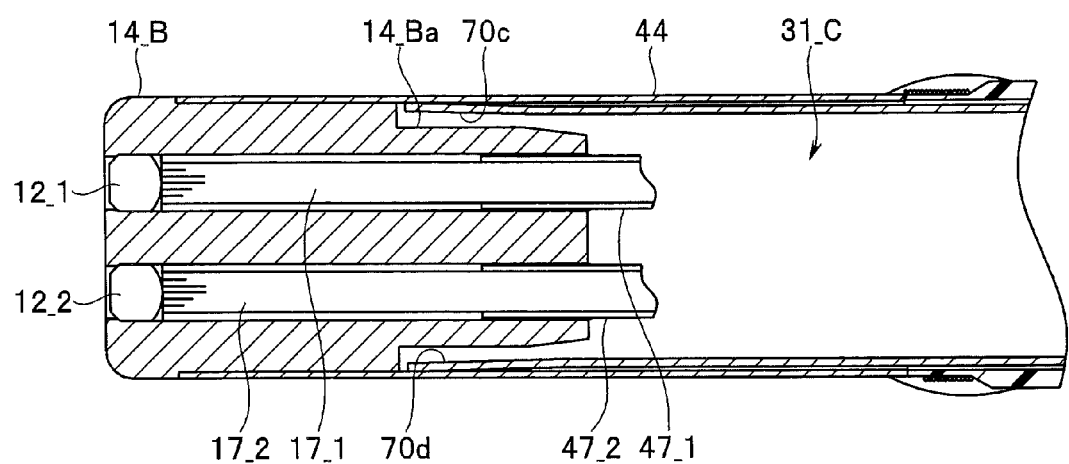
FIG. 29 relates to the fourth embodiment, and is an illustration diagram of the endoscope distal end side, which shows an assembled state of the nail-plate portion subjected to the bending processing in the outer radial direction.

As shown in FIG. 29, the nail-plate portions 70a, 70b which are expanded in advance in the outer radial direction are pressed by the inner wall surface of the sleeve 44. However, the distal end sides of the nail-plate portions 70a, 70b do not contact the outer circumferential surface of the fitting portion 14_Ba, and the nail-plate portions 70a, 70b hold the distal end bending piece 31_C with a pressing force generated between the nail-plate portions and the inner wall surface of the sleeve 44.

The fourth embodiment is capable of simplifying the fastening work before the assembling of the distal end bending piece 31_C, compared with the third embodiment. In addition, similarly as in the above-described embodiments, the fourth embodiment enables the metal members disposed on the exterior and inside of the endoscope to be surely and stably connected to the GND of the patient circuit 4a, to be equipotential with the GND, thereby capable of ensuring the electrical safety of the endoscope.

In the description of the first to fourth embodiments, the endoscope including the bending portion capable of bending the distal end portion of the insertion portion. However, the same configuration can be applied to a rigid endoscope including an insertion portion constituted only of a rigid portion. Specifically, a conductive component which can be fitted to the outside of the distal end portion and can be fitted also to the inside of a rigid tube is provided at a coupling portion between the distal end portion of the rigid endoscope and the rigid tube connected to the proximal end side of the distal end portion. If the nail-plate portion 33 according to the first embodiment is formed in the conductive component, for example, the nail-plate portion elastically presses the distal end portion and the rigid tube of the rigid endoscope at a predetermined contact pressure, to thereby capable of achieving a secure electrical conduction.

What is claimed is:

1. An endoscope comprising:
an insertion portion to be inserted into a subject;
a distal end rigid portion having conductivity and disposed on a distal end side of the insertion portion in an insertion axis direction;
a conductive component provided on a proximal end side of the distal end rigid portion in the insertion axis direction and coupled to the distal end rigid portion, the conductive component including an inner circumferential surface and an outer circumferential surface;
an electrical conductive portion formed on the conductive component, the electrical conductive portion including first and second protruding portions configured to be protruded inside the inner circumferential surface or outside the outer circumferential surface, the first protruding portion being elastically pressed against the distal end rigid portion; and
an exterior member which covers the distal end rigid portion and the conductive component, and is configured to be elastically pressed by the second protruding portion and electrically conductive with the distal end rigid portion through the electrical conductive portion.

2. The endo scope according to claim 1, wherein the electrical conductive portion elastically presses the distal end rigid portion in a radial direction at a predetermined contact pressure, to allow the distal end rigid portion and the conductive component to be electrically conductive with each other.

3. The endoscope according to claim 2, wherein the electrical conductive portion is formed by allowing a part of a distal end side of the conductive component covering the proximal end side of the distal end rigid portion to protrude in an inner radial direction.

4. The endoscope according to claim 3, wherein the electrical conductive portion is formed by a nail-plate portion which is formed by cutting out a part of the conductive component and allowing the cut-out part to protrude in the inner radial direction.

5. The endoscope according to claim 4,
wherein the nail-plate portion is formed by two cut pieces arranged symmetrically in the insertion axis direction and including open ends in the insertion axis direction, the two cut pieces are housed in a recessed portion provided on an outer circumferential side of the distal end rigid portion, and the distal end rigid portion and the conductive component are covered with the exterior member, and
wherein an inner surface of the exterior member is elastically pressed with one of the open ends of the two cut pieces, and a bottom surface of the recessed portion is elastically pressed with the other of the open ends of the two cut pieces, to allow the distal end rigid portion and the conductive component to be electrically conductive with each other.

6. The endoscope according to claim 4,
wherein the nail-plate portion is formed by two cut pieces continuously arranged in the insertion axis direction, a boundary part between the two cut pieces is flexed and housed in a recessed portion provided on an outer circumferential side of the distal end rigid portion, and the distal end rigid portion and the conductive component are covered with the exterior member, and
wherein an inner surface of the exterior member is elastically pressed by the two cut pieces, and a bottom surface of the recessed portion is elastically pressed with the flexed part between the two cut pieces, to allow the distal end rigid portion and the conductive component to be electrically conductive with each other.

7. The endoscope according to claim 4,
wherein the nail-plate portion is formed by two cut pieces arranged continuously in the insertion axis direction, a boundary part between the two cut pieces is flexed and housed in a recessed portion provided on an outer circumferential side of the distal end rigid portion, and the distal end rigid portion and the conductive component are covered with the exterior member, and
wherein an inner surface of the exterior member is elastically pressed with the cut piece on the base portion side of the two cut pieces, and a bottom surface of the recessed portion is elastically pressed with the cut piece on a distal end side of the two cut pieces, to allow the distal end rigid portion and the conductive component to be electrically conductive with each other.

8. The endoscope according to claim 4,
wherein the nail-plate portion is formed by a plurality of cut pieces arranged in a circumferential direction of the conductive component and including open ends in the insertion axis direction, the plurality of cut pieces are housed in a recessed portion provided on an outer circumferential side of the distal end rigid portion, and the distal end rigid portion and the conductive component are covered with the exterior member, and
wherein an inner surface of the exterior member is elastically pressed with the open ends of some cut pieces of the plurality of cut pieces, and a bottom surface of the recessed portion is elastically pressed with the open ends of other cut pieces of the plurality of cut pieces, to allow the distal end rigid portion and the conductive component to be electrically conductive with each other.

9. The endoscope according to claim 4,
wherein the nail-plate portion is formed by a protruding portion formed by allowing a wall surface of the conductive component to protrude in an arch shape toward inner radial side and a cut piece arranged on a lateral side in a circumferential direction of the protruding portion and including an open end in the insertion axis direction, the protruding portion and the cut piece are housed in a recessed portion provided on an outer circumferential side of the distal end rigid portion, the distal end rigid portion and the conductive component are covered with the exterior member, and
wherein an inner surface of the exterior member is elastically pressed with the cut piece and a bottom surface of the recessed portion is elastically pressed with the protruding portion, to allow the distal end rigid portion and the conductive component to be electrically conductive with each other.

10. The endoscope according to claim 1, wherein the conductive component is adhered and fixed to a member to be fixed to the distal end rigid portion at a position on a more proximal end side than the electrical conductive portion.

11. The endoscope according to claim 1, wherein the conductive component is a distal end bending piece located at a distal-most position of a bending portion that is provided on the proximal end side of the distal end rigid portion in the insertion axis direction and configured to be bendable by coupling a plurality of conductive bending pieces.

12. The endoscope according to claim 11, further comprising
an image pickup unit provided in the distal end rigid portion, for picking up an image of the subject,
wherein the bending portion is electrically connected to a reference potential which is common to the image pickup unit; and
the electrical conductive portion is formed by allowing a part of a distal end side of the distal end bending piece which covers the proximal end side of the distal end rigid portion to protrude in an inner radial direction, and the electrical conductive portion elastically presses the distal end rigid portion in a radial direction at a predetermined contact pressure, to allow the distal end rigid portion and the bending portion to electrically conductive with each other.

\* \* \* \* \*